(12) United States Patent
Grubb et al.

(10) Patent No.: US 8,806,944 B2
(45) Date of Patent: Aug. 19, 2014

(54) HIGH PRECISION ULTRASONIC CORROSION RATE MONITORING

(75) Inventors: Scott A. Grubb, Fulshear, TX (US);
David J. Blumer, Bartlesville, OK (US)

(73) Assignee: ConocoPhillips Company, Houston, TX (US)

(*) Notice: Subject to any disclaimer, the term of this patent is extended or adjusted under 35 U.S.C. 154(b) by 448 days.

(21) Appl. No.: 12/884,869

(22) Filed: Sep. 17, 2010

(65) Prior Publication Data

US 2011/0067497 A1 Mar. 24, 2011

Related U.S. Application Data

(60) Provisional application No. 61/243,869, filed on Sep. 18, 2009.

(51) Int. Cl.

| | | |
|---|---|---|
| *G01N 29/07* | (2006.01) | |
| *G01N 29/46* | (2006.01) | |
| *G01N 29/44* | (2006.01) | |
| *G01N 29/50* | (2006.01) | |
| *G01B 17/02* | (2006.01) | |
| *G01N 29/04* | (2006.01) | |
| *G01N 29/22* | (2006.01) | |
| *G01N 29/42* | (2006.01) | |
| *G01N 17/00* | (2006.01) | |

(52) U.S. Cl.
CPC .......... *G01N 29/223* (2013.01); *G01N 29/4454* (2013.01); *G01N 2291/101* (2013.01); *G01N 29/07* (2013.01); *G01N 29/50* (2013.01); *G01B 17/02* (2013.01); *G01N 29/043* (2013.01); *G01N 29/42* (2013.01); *G01N 29/46* (2013.01); *G01N 2291/044* (2013.01); *G01N 17/00* (2013.01); *G01N 2291/0258* (2013.01); *G01N 29/075* (2013.01)
USPC .............................................. 73/597; 73/602

(58) Field of Classification Search
CPC ..... G01N 29/075; G01N 29/42; G01N 29/46; G01N 29/07
USPC ............................................ 73/597, 602, 622
See application file for complete search history.

(56) References Cited

U.S. PATENT DOCUMENTS

| | | |
|---|---|---|
| 4,213,345 A | 7/1980 | Dufour |
| 4,428,237 A | 1/1984 | Zeger et al. |

(Continued)

OTHER PUBLICATIONS

K. Shivaraj, Krishnan Balasubramaniam, C.V. Krishnamurthy, and R. Wadhwan, "Ultrasonic Circumferential Guided Wave for Pitting-Type Corrosion Imaging at Inaccessible Pipe-Support Locations", Journal of Pressure Vessel Technology, vol. 130, 11 pages, May 2008.

*Primary Examiner* — Peter Macchiarolo
*Assistant Examiner* — Rose M Miller
(74) *Attorney, Agent, or Firm* — ConocoPhillips Company

(57) ABSTRACT

The invention relates to very precisely measuring changes in thickness of pipe walls to determine corrosion rate prior to any significant corrosion loss. The thickness is determined by ultrasonic testing where many measurements of the wall thickness are taken at the same spot by a fixed sensor and errors associated with noise and temperature changes are substantially eliminated. A highly sensitive receiver converts each reflected pulse to waves that are averaged with other pulse measurements. The resulting average wave is analyzed so that each waveform is analyzed to identify the extrema and inflection points of each reflected pulse. The resulting analysis provides a far more accurate determination of the time between reflected pulses. As a result, a far more accurate picture of corrosion at the location of the wall of the pipe can be determined within weeks with a high degree of confidence.

9 Claims, 3 Drawing Sheets

(56) References Cited

U.S. PATENT DOCUMENTS

| | | | |
|---|---|---|---|
| 4,658,648 A * | 4/1987 | Roddeck et al. | 73/597 |
| 5,557,047 A | 9/1996 | Koide | |
| 5,671,154 A * | 9/1997 | Iizuka et al. | 702/39 |
| 5,770,800 A | 6/1998 | Jenkins et al. | |
| 6,584,847 B1 * | 7/2003 | Hirose | 73/579 |

* cited by examiner

HIGH PRECISION ULTRASONIC CORROSION RATE MONITORING

CROSS-REFERENCE TO RELATED APPLICATIONS

This application is a non-provisional application which claims benefit under 35 USC §119(e) to U.S. Provisional Application Ser. No. 61/243,869 filed Sep. 18, 2009, entitled "High Precision Ultrasonic Corrosion Rate Monitoring," which is incorporated herein in its entirety.

STATEMENT REGARDING FEDERALLY SPONSORED RESEARCH OR DEVELOPMENT

None.

FIELD OF THE INVENTION

This invention relates to monitoring corrosion rates for metals and especially monitoring corrosion rates for pipelines.

BACKGROUND OF THE INVENTION

In the process of conveying fluids in pipelines, it is common to provide chemical treatments or other means to limit the rate of corrosion and monitor the pipeline to make sure that the corrosion inhibition program is effective. Monitoring corrosion rates have historically been accomplished by intrusive pipe or vessel wall penetrating instruments and/or metal coupons that are carefully weighed prior to installation and once again after retrieval. The instruments and coupons alter the internal flow of the fluids around or through the measuring devices which potentially generates environments less or more severe than if they were not present. Such conditions can produce corrosion data that is misleading. Further, while some coupons are made from the same materials as used in the construction of the pipe line or vessel, exact metallurgical replication of the material is suspect as well. In addition, local area galvanic and scale affects may not be suitably reproduced on the small surface area electronic probes. Typically, the coupons are withdrawn for measurements such as weight loss and the recovery of these instruments from an operating vessel or pipe requires special tools and careful procedures. If the corrosion rate is higher than expected, coupons have been lost inside the vessel or pipeline creating additional issues. Additionally, intrusive probes have a useful life and therefore must also be removed if another device is to takes its place and continue to provide the monitoring.

In addition, operating pipelines are often installed in places not easily accessible, perhaps by weather such as in the arctic, and regular access and monitoring get quite complicated. And once metal in the pipe has been corroded or pitted, the lost metal does not come back. For readily understandable cost issues related to buying extra thick and heavy pipe, transporting extra thick and heavy pipe to the pipeline location and welding and installing extra thick and heavy pipe, pipelines are generally not constructed with a lot of extra thickness. As such, early detection of an ineffective corrosion inhibitor program is important for long term use of the pipeline.

Such issues were broadly revealed to the public in the news reports of the 2006 leaks in the pipelines in Prudhoe Bay, Ak. where unexpectedly high corrosion was found and the pipeline was taken out of service for months while many miles of pipe had to be replaced. The time period during which the inside of pipeline was not inspected by a pipeline inspection gauge ("pig") was too long and other testing technologies were not used on the pipe. The operator trusted the corrosion control protocols for the pipeline without double checking the corrosion rate with adequate measurements. Running a pig is not a simple or low cost exercise and other techniques for monitoring corrosion techniques are highly desired.

One non-invasive technique for measuring corrosion is an ultrasonic measuring device which directs ultrasonic energy into the pipeline. As the sensor receives reflections from the back or inside wall of the pipe and the elapsed time from sending to receiving, or two or more sequential backwall echoes, provides a measure of the wall thickness at that location. Currently, field use ultrasonic sensors are primarily handheld devices allowing for many measurements at diverse locations, but only taken on a periodic basis. Such sensors provide an accuracy of up to about plus or minus 1 mil (0.001 inches) and is typically quoted at an accuracy of plus or minus 10 mils by corrosion engineers. While this may sound accurate, a pipe having a thickness of ¼ inch is only 250 mils thick. A pipe with ⅛ inch wall is only 125 mils thick. The Prudhoe Bay pipe was ⅜ inch thick and was found to be approximately 70 to 80 percent corroded. Pipes for pipelines are not made with high precision, and as such, the thickness of pipes vary by several mils immediately after manufacture in all directions (along length and around the periphery. As such, measureable corrosion is generally not detected by two successive measurements of a handheld device due to measurements at slightly different locations, by different personnel and possibly at different temperatures until at least 10 mils of pipe thickness is lost and as much as 20 or more mils of wall thickness are actually lost. Clearly, it would be more desirable to identify unacceptable loss or an unacceptable loss rate at a much earlier time frame before much damage is sustained.

SUMMARY OF THE INVENTION

The invention more particularly includes a process for precisely measuring a thickness of a sound conducting material where the process comprises installing an ultrasonic sensor to a location of the sound conducting material where the ultrasonic sensor includes an ultrasonic source disposed to provide an ultrasonic pulse into the material, and ultrasonic receiver disposed to receive reflections of the ultrasonic pulse from the opposite side of the material. A temperature sensor and analytical circuitry are arranged to receive and collect temperature data from the temperature sensor and waveform data from the receiver. The temperature of the material is measured while a series of pulses is emitted from the ultrasonic source into the material. The first and second reflections and perhaps more reflections of each pulse are received by a receiver where the reflections have crossed the thickness of the material to create a waveform and a number of waveforms are collected into a Sample Collection. The waveforms within the Sample Collection are aligned and the aligned Sample Collection is averaged to create a Representative Waveform for that Sample Collection. At least the first and second echo sets are identified within the Representative Waveform representing the first reflection from the material and second reflection from the material, respectively and landmark characteristics points of each backwall echo are also identified. The landmark characteristic points of each backwall echo are averaged in some way to calculate a representative location of that backwall echo and the thickness of the material is determined based on half the elapsed time between these representative locations of the successive echoes.

The invention may further include having the sound conducting material being a metal wall of a vessel or pipe exposed to varying temperatures on at least one of the inside or outside and wherein the step of calculating a coefficient of thermal velocity expansion for the metal wall is determined by collecting a number of Sample Collections at different temperatures and performing a regression analysis for the various thickness measurements at the temperature of the respective Sample Collections to find a coefficient of thermal velocity expansion for the metal wall and thereafter provide temperature corrected thickness measurements of the metal wall.

In another aspect, the invention may further include identifying any outlier waveforms that are substantially different than most wave forms in the Sample Collection and eliminating the outlier waveforms from the Sample Collection before the Representative Waveform is created for the Sample Collection.

In a more specific view of the invention for precisely determining corrosion rate of a metal wall of a vessel or pipe, an ultrasonic sensor is installed to a location of the wall where the ultrasonic sensor includes an ultrasonic source disposed to provide an ultrasonic pulse into the wall, and ultrasonic receiver is disposed to receive reflections of the ultrasonic pulse from the opposite surface of the wall material, and a temperature sensor and analytical circuitry to receive and collect temperature data from the temperature sensor and wave form data from the receiver. The temperature of the wall is measured and a series of pulses from the ultrasonic source are emitted into the wall. At least a first and second reflection of each pulse from the wall that has crossed the thickness of the wall are received with a receiver to create a waveform and collecting the waveforms into a Sample Collection. The temperature of the wall is measured at the beginning and the end of the period for collecting the data of the Sample Collection. The Sample Collection may be eliminated if it is found that the temperature has not remained substantially constant during the collecting of the Sample Collection. The waveforms of the Sample Collection are then aligned and averaged to create a Representative Waveform for that Sample Collection. At least the first and second echo sets within the Representative Waveform are identified representing the first reflection from the material and second reflection from the material, respectively. Extrema and inflection points of each echo are determined and the "centers" of each echo using the characteristic points are determined. Then the elapsed time between sequential echoes is calculated through the difference in their "centers". A coefficient of thermal velocity expansion for the metal wall and a particular ultrasonic transducer for that particular mounting is calculated by collecting a number of Sample Collections over time and at different temperatures and performing a regression analysis for the various thickness measurements at the temperatures of the respective Sample Collections. Then a temperature corrected wall thickness of the material is determined based on the calculated average time for an ultrasonic sound wave to travel through the wall along with the coefficient of thermal velocity expansion in a suitable temperature compensation model. Further Sample Collections are taken over time to measure the wall thickness at subsequent times and compare the subsequent temperature corrected wall thickness measurements to determine a corrosion rate for the wall.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

Turning now to the preferred arrangement for the present invention, reference is made to the drawings to enable a more clear understanding of the invention. However, it is to be understood that the inventive features and concept may be manifested in other arrangements and that the scope of the invention is not limited to the embodiments described or illustrated. The scope of the invention is intended only to be limited by the scope of the claims that follow.

According to the present invention, extensive monitoring of a pipeline even when such a pipeline is inaccessible for long periods of time such as during the winter in the arctic. Extensive monitoring is accomplished by one or more, preferably many more, sensors that are mounted to the pipeline for extended measurements. Preferably, such sensors are ruggedly constructed to endure harsh weather, vibrations, bumps and even animal hazards. It is preferable to locate sensors where corrosion will most likely occur, but corrosion is typically inconsistent along the length of the pipeline and occurs as both thinning and as pits. Having the ability to provide many sensors on a pipeline would allow sensors to be located primarily along the top of the pipeline, along the bottom of the pipeline, at low portions along the pipeline, and at bends and turns in the pipeline. As such, the many individual sensors may be spaced along the pipeline to provide an array of data that will most likely provide a precise indication of the corrosion loss for the whole pipeline and provide better corrosion inhibitor management of the pipeline.

Figure 1:
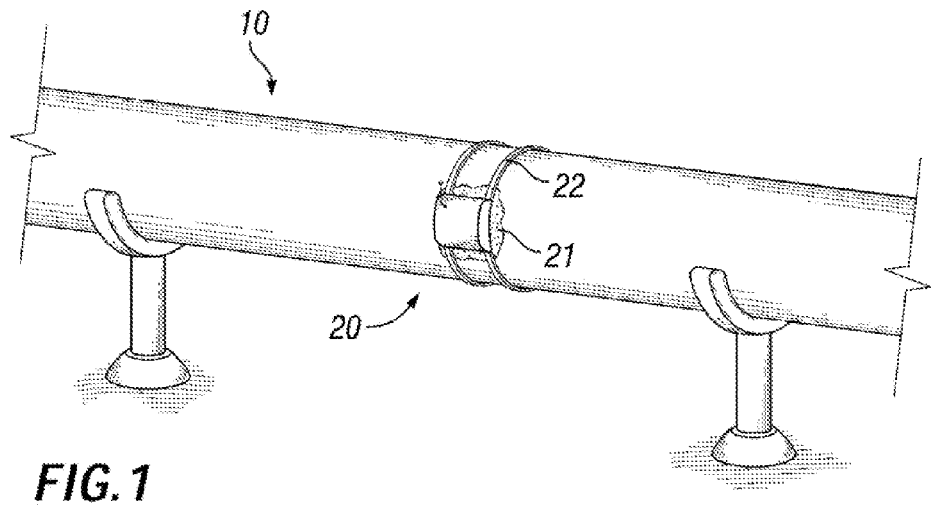
FIG. 1 is fragmentary perspective view of a pipeline with a ultrasonic sensor attached thereto in accordance with the preferred arrangement of the invention.

In FIG. 1, an ultrasonic sensing device generally indicated by the arrow 20 is shown attached to the outside of a pipe 10. The pipe 10 is cleaned of debris and anything that might interfere with the precision ultrasonic measurements prior to the installation of the ultrasonic sensing device 20. Conductive paste 21 is applied to the outside thereof prior to placing the ultrasonic sensing device 20 on the pipe 10. Conductive paste 21 provides conduction of sonic pulses into and out of the pipe 10 where an air gap would impede sonic conduction. Steel bands 22 are shown wrapped around the pipe 10 to firmly hold the ultrasonic sensing device 20 in place. Adhesives and any other suitable hardware may also be used to bond or secure the ultrasonic sensing device to pipe 10.

Figure 2:
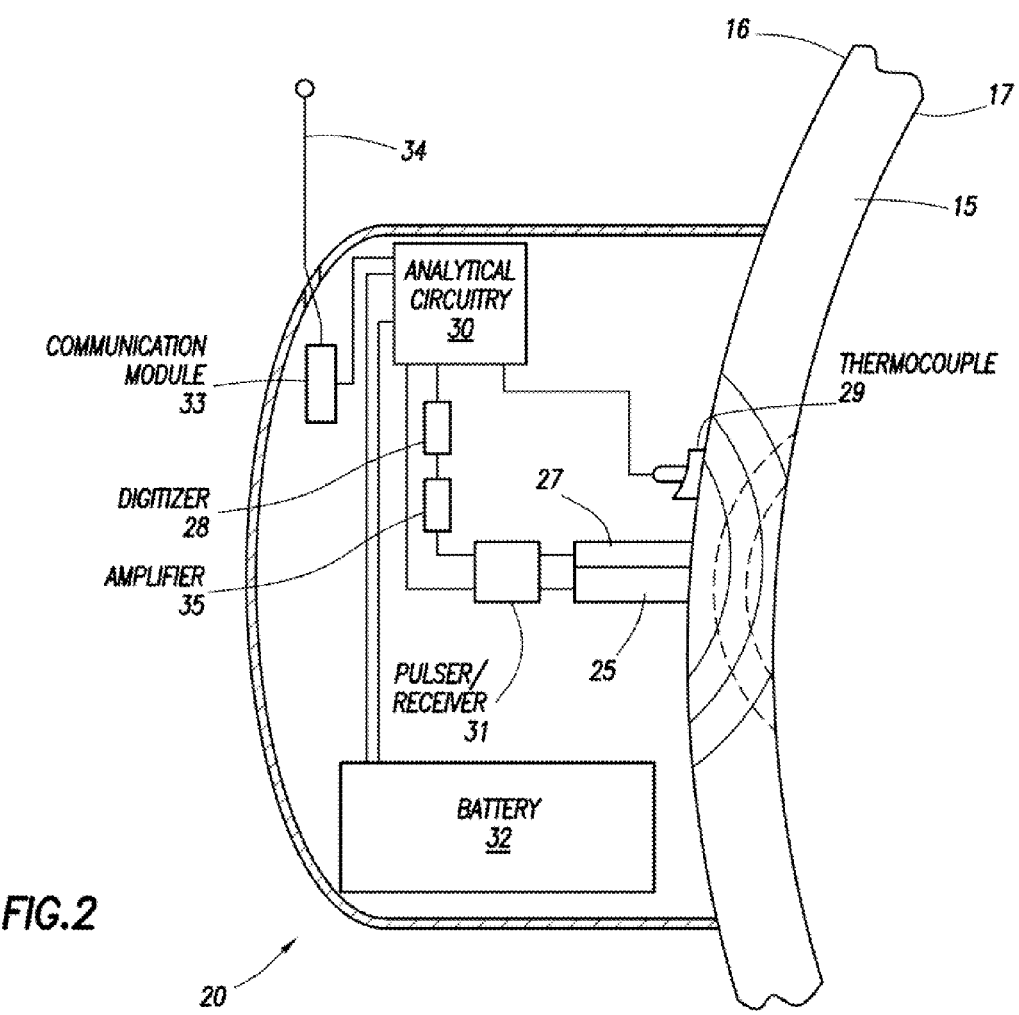
FIG. 2 is a fragmentary cross section with the internals of the ultrasonic sensor shown schematically.

In FIG. 2, the pipe 10 is seen to comprise a wall 15 with an outer surface 16 and an inner surface 17. Ultrasonic sensing device 20 is mounted in contact with the outer surface 16 with conductive paste 21. Ultrasonic sensing device 20 includes a source 25 and a receiver 27 along with a pulser/receiver 31, amplifier 35 and digitizer 28 to convert the signal generated by the receiver 27 from analog to digital. The signal provided by 27 is likely to be quite weak and is preferably amplified by amplifier 35 prior to digitizing by digitizer 28. Analytical circuitry 30 is arranged to analyze the digitized signal received by receiver 27. Analytical circuitry 30 may take many forms such as a computer or a more specialized processing system such as a field-programmable gate array (FPGA). A highly sensitive thermocouple 29 measures the temperature of the wall 15 and also provides that data to the analytical circuitry 30. Other accurate temperature measuring devices including a resistance temperature detector (RTD) or a thermistor may be used in place of the thermocouple 29. A battery 32 may be provided to power the ultrasonic sensor 20 and communication module 33 along with antenna 34 may be provided so that corrosion rate information may be provided remotely to operating personnel or perhaps some portion of the data analysis may be accomplished remotely from the ultrasonic sensor 20. In operation, the source 25 provides a sonic pulse that crosses through the conductive paste 21 and into the wall 15 through the outer surface 16 of the pipe 10. As the pulse impacts with each of the surfaces 16 and 17, some amount of the energy of the pulse radiates from the wall 15 and some is reflected back across the wall 15. Arcs are drawn in solid lines within the wall 15 to provide a representative indication of the pulse passing through the wall 15 and in dashed lines for those reflecting from the inner surface 17 back toward the outer surface 16. So, when the source 25 emits a pulse, a reflection from the inner surface 17 passes back to the outer surface 16 to be received by the receiver 27 and, at the same time, a portion is reflected back to the inner surface 17. The pulse reflects back and forth while the receiver 27 continues to receive signals of the pulse. Eventually the reflections dissipate and fade into the "noise" continuously received by receiver 27. The signal received at the receiver 27 is provided to analytical circuitry 30 and is recorded as a digitized wave as presented in FIG. 3.

Figure 3:
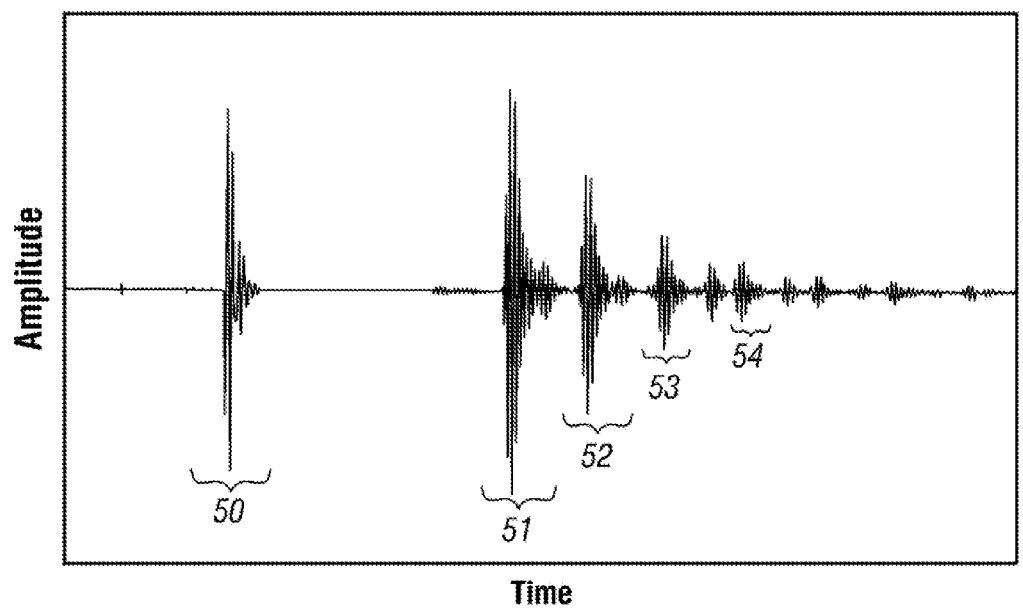
FIG. 3 is a chart showing a representative wave form received from a pipe.

In FIG. 3, the initial pulse is indicated by bracket 50, the first received reflected pulse is indicated by bracket 51, the second received reflected pulse is indicated by bracket 52, the third received reflected pulse is indicated by bracket 53 and the fourth received reflected pulse is indicated by bracket 54. Precisely measuring the time from the first reflected pulse 51 to the second reflected pulse 52 provides a precise indication of the current thickness of the wall 15 of the pipe 10. There are two points to be made at this point. First, each pulse actually comprises a highly detailed waveform with many extremas or local maximums and minimums and each pulse is not precisely mirrored by the second reflection. Current precision of between plus or minus 1 to 10 mils of wall thickness relies on a general interpretation of the reflected pulses and the time difference. In the present invention, the highly detailed waveform is more deeply analyzed and far greater precision of wall thickness may be determined as a result.

The inventors have also validated that high precision may be obtained by measurements of the time between the first, second and third reflections again utilizing the wave form analysis of the present invention. Measurements of the time between the initial pulse of the ultrasonic sensor to the first backwall echo can also be used to determine the time of flight for thickness calculations. This method includes circuitry to take into account the delay between the time the digitizer senses the initiating pulse and the time that the initiating pulse excites the ultrasonic element. This delay will cause a bias in the calculated wall thickness. The inventors prefer to measure the time between two sequential backwall echoes. This process is simple in that it does not require additional circuitry or algorithm steps to eliminate the delay.

Ultrasonic sensors suitable for this invention include single and dual element sensors. Single element sensors suffer from "ring down", a consequence of the excitation voltage applied over less than 100 ns at a level of 100 to 300 volts DC. Single element sensors perform as both the initiator and receiver of the ultrasonic wave. The initial high voltage shock to the ultrasonic sensor highly excites the element requiring substantial time to recover and return to its typical zero signal level. This time period may not be short enough to recover fully before the first backwall echo returns to the ultrasonic sensor, resulting in the reflected energy being detected before the sensor has recovered. Thus, the waveform of a single element ultrasonic sensor can include the exponential decay of the original pulse with the backwall echo pulses overlaid where the decaying original pulse masks at least some portions of the backwall echo. Dual element ultrasonic sensors are preferred as they do not suffer from "ring down" due to the division of labor between delivering the initial impulse and sensing the backwall echoes. One element receives the initial high voltage pulse from analytical circuitry 30 and generates the ultrasonic wave. The second element, which is acoustically isolated, will sense and receive the reflected waves. This arrangement optimizes the clarity of the reflection waveform for processing. Both elements are typically within the same housing.

It should also be noted that the goal for measuring corrosion is precision as compared to accuracy. In other words, the corrosion rate is key and a device that can precisely indicate small changes in metal thickness is of highest importance. While it is important to know that the wall is sufficiently thick for safety purposes, knowing its dimension to the plus or minus 0.000001 inches is not critical. But knowing that the wall of the pipe has changed in thickness by more or less than 0.000001 inches in two weeks can be very helpful in properly and efficiently administering a corrosion inhibiting program, providing early detection of a change in corrosion rate, and ultimately assuring the long term operation of the pipeline. So precision is the key and variability undermines precision.

Turning back to FIG. 3 and as noted above, to obtain the precision desired and that is available, one must precisely measure the time between two pulses that each have some level of "blurriness" associated with them. Each pulse, at the time scale necessary for the desired precision, has a long time duration. So, the invention includes a precise determination of where within each echo that we can precisely identify the time the echo "arrived". For comparison sake, one mil of thickness will mean the time difference of 0.004 µs. Accuracy of plus or minus 0.1 mils requires time measurements to plus or minus 0.0004 µs. For purposes of the present invention, accuracy to plus or minus 0.001 mils or 0.000001 inches requires precise time measurements down to within 0.000004 µs. These times are all based on a material with an ultrasonic velocity of 230 mils/µs; a value typical for steel.

For the inventors, the key to high precision is the analysis of the underlying waveform received by the receiver. The waveform is analyzed as a piecewise smooth wave to digitally determine the extrema and the inflection points for each echo within the waveform. However, at the targeted precision for this invention temperature has a profound effect on the ultrasonic wave velocity and also an effect on the thickness of the metal based on thermal expansion of metal. Thus, the temperature of the metal in wall 15 must be known.

Figure 4:
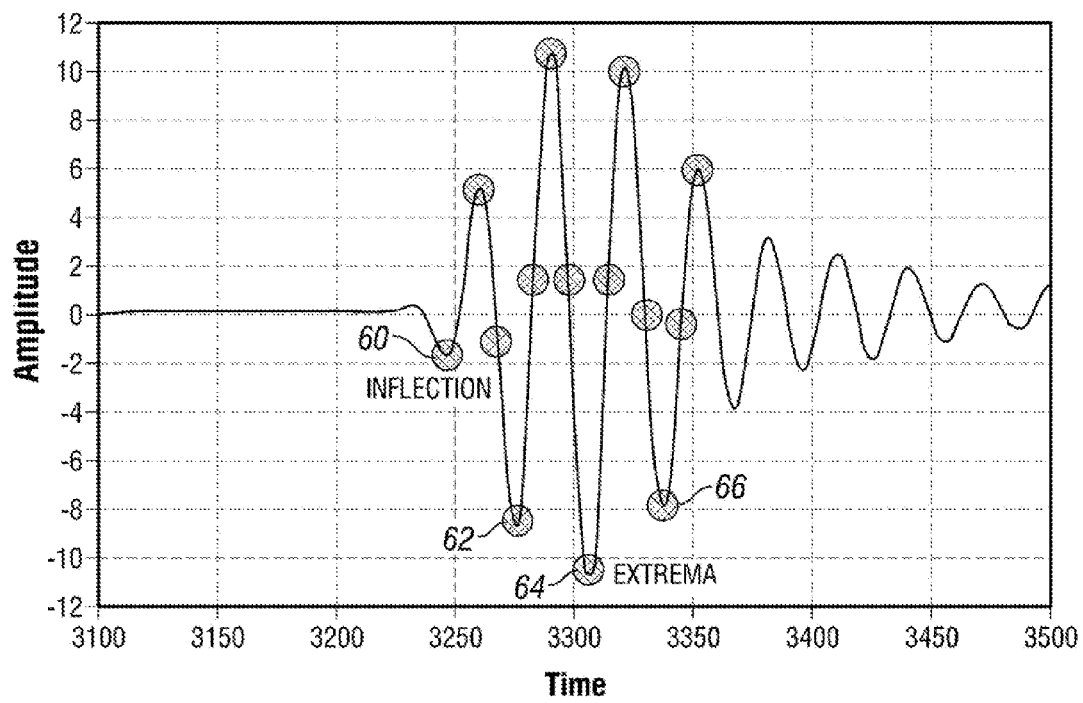
FIG. 4 is a chart showing some aspects of the analysis of a wave form for precisely determining the thickness of a pipe.

Temperature affects can be accounted for once the precise coefficient of thermal velocity expansion is determined and the analytical circuitry includes that function. So the invention includes the installation of the ultrasonic sensor 20 to the pipeline 10 or vessel or whatever metal object that one wants to measure for metal loss over time. Once installed, the sensor 20, along with the thermocouple 29, begins to generate data that will provide a precise relative thickness change of the wall 15 and the coefficient of thermal velocity expansion of the wall 15. The data is preferably created in sets, or a Sample Collection, where a number of pulses are delivered to the wall 15 and each echo is received as a waveform and recorded within the memory of the analytical circuitry 30. As noted above, the analytical circuitry 30 uses a digitized waveform for storage and analysis. A detailed explanation of digitizing waveforms is not considered necessary as this is known technology. The temperature is recorded over the period in which the Sample Collection is collected and the entire Sample Collection may be rejected if the temperature has markedly changed over the time of collection of the Sample Collection. For a Sample Collection that is collected during a stable temperature time frame all the waveforms are averaged together to create a single Representative Waveform, which will then be used to digitally identify each extrema and each inflection point of each backwall echo. This analysis can include filtering out poor waveforms based on various criteria, alignment of the waveforms to minimize recording start offsets, and smoothing and averaging of acceptable waveforms. FIG. 4 provides a visual presentation of the waveform with the extremas and inflection points identified. It is not uncommon to have outlier waveforms within a Sample Collection and when such outliers are identified as being substantially different than most other wave forms they may be filtered or eliminated from the Sample Collection. Preferably, a Sample Collection is collected over a compact period of time and would preferably include up to many thousands of individually initiated and captured waveforms. Typically a Sample Collection is obtained within a few seconds.

Preferably, once the Sample Collection is acquired, the temperature over the collection time is verified to have remained consistent. Variations may be accommodated with more complicated analytical circuitry 30, however, simplicity is preferred and any Sample Collection with a significant temperature variation is preferably eliminated.

Each backwall echo waveform with the Sample Collection is analyzed to align all of the waveforms to each other. In other words, most of the echo waveforms will appear almost identical to the human eye if they are aligned so as not to be offset to the "left" or "right". Due to recording start offsets and/or variance in the electrical components, etc., some waveforms may be slightly displaced time wise from other waveforms. Aligning the waveforms brings additional precision to the analysis. Aligning is done by analyzing each waveform to find one or more key landmark characteristic points and overlaying each waveform so that the landmark characteristic points are precisely aligned.

One method to align the waveforms is analyze each waveform to identify the second negative peak 64 of the first echo. For example, in FIG. 4, the first criterion may be to identify the most negative peak 64 in the waveform across a time period where the first echo should be found. The second step is to identify the most negative peak 62 immediately ahead of the overall most negative peak 64 and from this point identify the next prior negative peak 60. A last peak is identified as the negative peak 66 that occurs after the most negative peak 64. Comparing all of these peaks to predetermined proportional relationships and/or a static threshold amplitude, since peak 62 has an amplitude so much greater than peak 60 and fairly close to peak 64, and peak 66 has an amplitude close to peak 64, peak 62 is therefore identified to be the first negative peak and peak 64 is the second negative peak of the echo. The second negative peak 64 is used as the alignment point for all the waveforms within the Sample Collection.

It should be noted that although the waveform is an analog signal, it must be digitized with sufficient precision to discern a reasonably accurate portrayal of the underlying analog signal. The more rapid the digitizer samples the analog signal, the more accurate and smoother; the digital waveform will appear as long as a reasonable number of bits are used in the measurement. With all of the waveforms aligned, the waveforms may be ordered based on the magnitude of the pointwise squared difference between each particular waveform and the average of all the remaining waveforms. Whatever the basis for ordering, the ordering may be such that the lowest magnitudes are at one end of the order and the highest magnitudes are at the other end. Any waveform that would likely be deemed an outlier would be ordered at one end or the other of the ordered Sample Collection. The Sample Collection could then be filtered by removing a preselected portion at the ends of the order to remove outliers. Clearly, non-outliers would be eliminated also, but it is preferred that less than 10 percent be removed and that thousands of waveforms would remain that would provide valid and precise measurements of the thickness of the wall 15. It should be noted that filtering is not necessary, but may be useful and the suggested method shows computational speed advantages.

With the Sample Collection now aligned and filtered, a Representative Waveform is created by averaging each digital component of all of the waveforms in the Sample Collection. The Representative Waveform is essentially an average of all of the waveforms and provides a single waveform for analysis of the current thickness of the wall 15. This Representative Waveform then becomes the subject of analysis to identify the key landmark characteristic points within. Referring to FIG. 4, all of the extremas are identified and the inflection points are precisely identified. The extremas are identified as the local maximum and minimum points on the echo portion of the waveform. For the inflection point, the point that most precisely locates where the curve changes curvature from one direction to curvature in the other direction between a local maximum and minimum is the inflection point.

With the first echo identified, the first echo is compared with a portion of the Representative Waveform following the first echo that is also the same length of time as the first echo with the goal of finding a second echo. Now, it must be remembered that a machine is performing this analysis using numbers and not actually stepping back and looking at the nice waveform illustrated in FIG. 4. While it is easy for a human to step back and see the first echo 51 and second echo 52 in FIG. 3, the analytical circuitry precisely "finds" the second echo by taking a segment of the waveform further down the line from the first echo and comparing it to the first echo by calculating the cross-correlation between the two data sets. A large cross-correlation result indicates a significant match and a small result means that there is a poor correlation between the compared data sets. The first backwall echo will have a duration encompassing the entire echo response and is represented by a finite number of sequential discrete data points from the waveform. Comparison of this set of discrete data points against equally sized sets of discrete data points sampled from the same waveform further out in time using the cross-correlation technique results in positive and negative values. Stepping the comparison set one, or more, data points per cross-correlation iteration through enough of the remaining waveform to cover the next backwall echo will generate a set of values that can be searched for a maximum. This maximum positive cross-correlation value will represent the location of maximum likelihood for the next backwall echo. Subsequent backwall echoes are located using the same sequence with the alteration that the first backwall echo used in the cross-correlation comparison is the last one detected.

Once all backwall echoes have been located the entire waveform will be transformed using the Discrete Fourier Transform using the Fast Fourier Transform algorithm. This is done to calculate the transform coefficients, which will be used in the application of the first and second derivatives of the Inverse Discrete Fourier Transform to extract the first and seconds derivatives at the discrete data points of each backwall echo. Determination of extrema and inflection points can be achieved through the use of derivatives. These extrema and inflection points are the landmark characteristic points necessary to identify the time that an echo was received. An extrema will be located where the first derivative is equal to zero indicating the crest of a hill of the pit of a valley. An inflection point will be located where the second derivative has a change in sign identifying a change in concavity. Various other functions could be fitted to the entire or portions of the backwall echo portion of the waveform and then their derivatives taken to locate extrema and/or inflection points. However, this fitting approach will have its precision limit as that of the first and second derivatives of the Inverse Discrete Fourier Transform, meaning that no other method will give any better values of the extrema and inflection point than the one used here, and they will likely add variance to the results.

A representative point is located for the various backwall echoes through a central weighted average of all or some of the extrema and inflection points within an echo. Calculation of the time span between sequential backwall echoes is simply the difference in time between the centrally weighted averages of the extrema and inflection points of each echo. Thus, each echo is reduced to a representative point and the time between the two representative points of the first and second echoes is the precise time it takes for sound to travel through the thickness of the wall 15, twice. The thickness is one half the time between echoes multiplied by the speed sound travels through the specific metal, at the measured temperature, that comprises the wall 15.

The process is repeated where a variety of Sample Collections are collected at a variety of different temperatures, preferably over the next few days or weeks. The coefficient of thermal velocity expansion may then be calculated by examination of the calculated thickness measurements in a regression analysis. The preferred regression algorithm is the Nelder-Mead Simplex algorithm, however any suitable regression scheme may be used. The coefficient of thermal velocity expansion as determined by the regression analysis is then used to determine a Temperature Compensated Thickness Measurement from any suitable model.

At future times, whether weeks later or months later, further Sample Collections are collected to determine Temperature Compensated Thickness Measurements that are provided to operation personnel and recorded for future reference. With a series of Temperature Compensated Thickness Measurements taken over time, differences in thickness over the time for which the Sample Collections were collected provide a rate of loss. The rate of loss, if low, will verify that the corrosion inhibition programs are effective and, if not low, should be considered for adjustment.

Operation personnel are best advised of the efficacy of the corrosion inhibition program by having corrosion rate data from a number of locations along the pipeline as one or a few locations may not be representative of what is occurring in the entire pipeline, but higher confidence is attained by data from more locations along the pipeline. As such, it is preferred that a plurality of ultrasonic sensors 20 are installed along the pipe 10 and remotely monitored.

Figure 5:
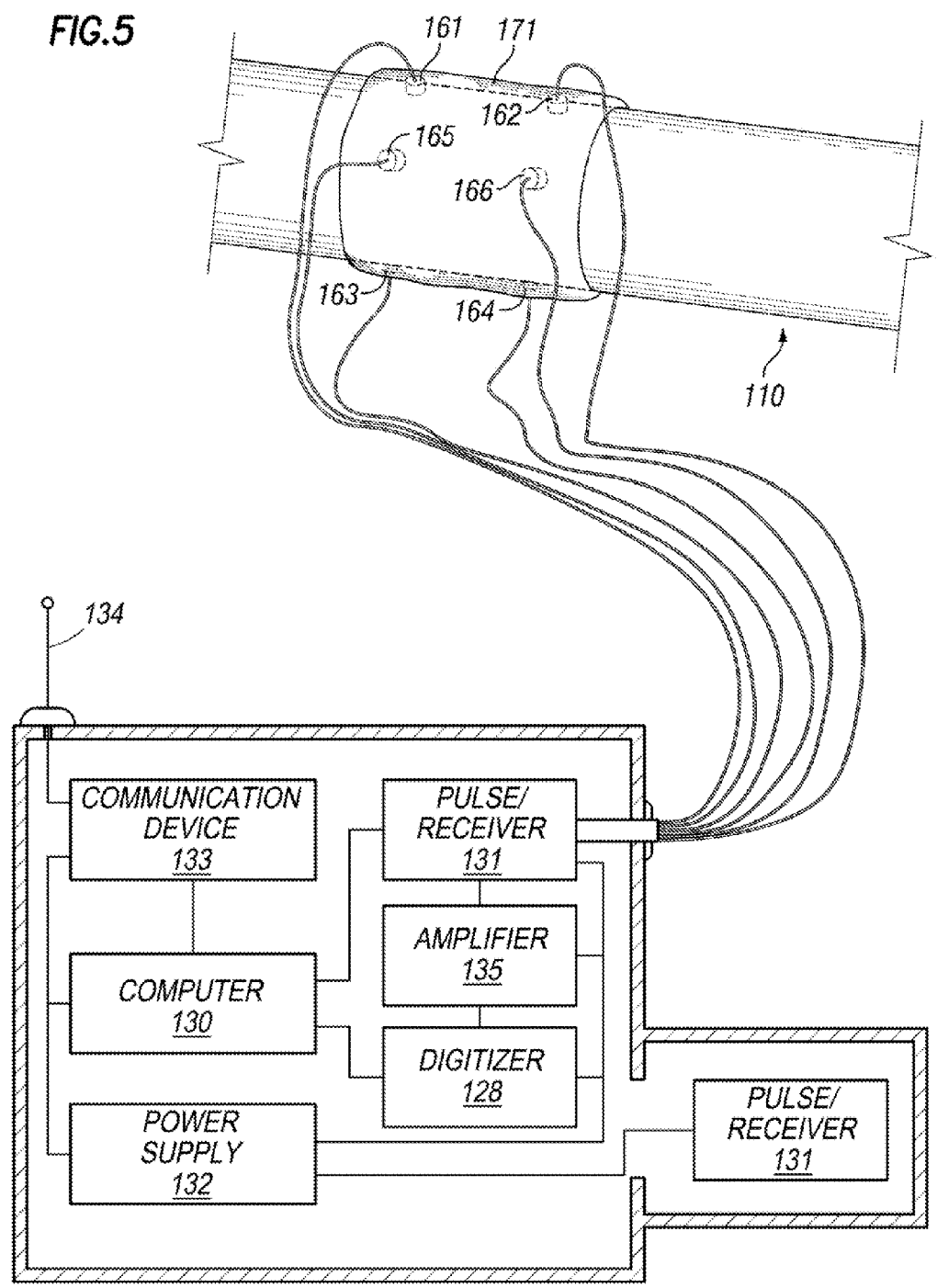
FIG. 5 is a block diagram of several elements of the invention shown in relationship to a pipeline.

In a further aspect of the present invention, it has been recognized that precision of measurements is impacted by the temperature of the amplifier 32 and digitizer 28. As such, in FIG. 5, an additional embodiment of the present invention is shown where the pulser/receiver 131, amplifier 135 and digitizer 128 are contained in an insulated housing 138 with temperature controlling equipment 136 to maintain the temperature within housing 138 to remain within a preferred temperature range. Actually, the specific temperature is not critical as much as it is preferred that the temperature be very consistent from measurement to measurement. In the preferred arrangement as shown in FIG. 5, the power supply 132, computer 130 and communication device 133 are also included in the housing. As long as the volume within the housing is small, it is believed that conventional temperature controlling technology is available to maintain the temperature with one degree Fahrenheit and more preferably within one half a degree Fahrenheit and even more preferably within 0.2 degrees Fahrenheit from measurement to measurement over a period of months or years that is consistent regardless of sun exposure, season, whether day or night.

The pulser/receiver 131 may also be multiplexed to take measurements from several locations. As shown, sensors 161 and 162 are arranged along the top of the pipe 110 with sensors 163 and 164 at the bottom of the pipe 110. Sensors 165 and 166 may provide measurements at the side of the pipe 110 and the temperature of the pipe 110. The pipe 110 is shown with insulation 171 overlying the sensors 161-166 to minimize temperature changes while Sample Collections are being collected.

Finally, the scope of protection for this invention is not limited by the description set out above, but is only limited by the claims which follow. That scope of the invention is intended to include all equivalents of the subject matter of the claims. Each and every claim is incorporated into the specification as an embodiment of the present invention. Thus, the claims are part of the description and are a further description and are in addition to the preferred embodiments of the present invention. The discussion of any reference is not an admission that it is prior art to the present invention, especially any reference that may have a publication date after the priority date of this application.

The invention claimed is:

1. A process for precisely measuring a thickness of a sound conducting material where the process comprises:
   a) installing an ultrasonic sensor to a location of the sound conducting material where the ultrasonic sensor includes an ultrasonic source disposed to provide an ultrasonic pulse into the material, an ultrasonic receiver disposed to receive reflections of the ultrasonic pulse from the opposite side of the material, a temperature sensor and analytical circuitry to receive and collect temperature data from the temperature sensor and waveform data from the receiver;
   b) measuring the temperature of the material;
   c) emitting a series of pulses from the ultrasonic source into the material;
   d) receiving at least a first and second reflection of each pulse from the material that has crossed the thickness of the material with a receiver to create a wave and collecting the waveforms into a Sample Collection;
   e) aligning the waveforms within the Sample Collection;
   f) averaging the set of aligned waveforms within the Sample Collection to create a Representative Waveform for the Sample Collection;
   g) identifying at least first and second echo sets within the Representative Waveform representing the first reflection from the material and second reflection from the material, respectively;
   h) transforming each backwall echo using a Discrete Fourier Transform;

i) determining extrema and inflection points of each transformed backwall echo by performing an Inverse Discrete Fourier Transform;

j) averaging all or some of the extrema and inflection points of each backwall echo to calculate a representative location of the backwall echo; and k) determining the thickness of the material based on the precise time for an ultrasonic sound wave to travel through the material.

2. The process for precisely measuring the thickness of a sound conducting material according to claim 1 wherein the sound conducting material is a metal wall of a vessel or pipe exposed to varying temperatures on at least one of the inside or outside and wherein the process further includes the step of calculating a coefficient of thermal velocity expansion for the metal wall by collecting a number of Sample Collections at different temperatures performing a regression analysis for the various thickness measurements at the temperature of the respective Sample Collections to find a coefficient of thermal velocity expansion for the metal wall and thereafter provide temperature corrected thickness measurements of the metal wall.

3. The process for precisely measuring the thickness according to claim 2 further comprising collecting Sample Collections over an extended period of time to determine a corrosion rate for the metal wall.

4. The process for precisely measuring the thickness according to claim 3 wherein the corrosion rate is communicated to a location remote from the ultrasonic sensor.

5. The process for precisely measuring the thickness according to claim 2 wherein the regression analysis is a Nelder-Mead Simplex algorithm regression analysis.

6. The process for precisely measuring the thickness according to claim 2 further including the step of maintaining the temperature of the analytical circuitry within a range of one degree Fahrenheit for all measurements.

7. The process for precisely measuring the thickness according to claim 1 wherein each Sample Collection is analyzed to identify any outlier waveforms that are substantially different than most wave forms in the Sample Collection such that any outlier waveforms are eliminated from the Sample Collection before the Representative Waveform is created for the Sample Collection.

8. The process for precisely measuring the thickness according to claim 1 further including the step of maintaining the temperature of the analytical circuitry within a range of one degree Fahrenheit for all measurements.

9. The process for precisely measuring the thickness according to claim 1 wherein the ultrasonic receiver disposed to receive reflections of the ultrasonic pulse from the opposite side of the material provides a signal to the analytical circuitry comprising data of the first and second reflection of each pulse received from the material and wherein the analytical circuitry further includes an amplifier for amplifying signal and a digitizer for digitizing the signal and the process further comprises maintaining the temperature of the amplifier and digitizer within a range of one half of one degree Fahrenheit for all measurements.

* * * * *